United States Patent [19]

Langdon

[11] Patent Number: 5,386,735
[45] Date of Patent: Feb. 7, 1995

[54] APPARATUS FOR COLLECTING A FLUID SAMPLE FROM A PATIENT AND CONTAINER FOR STORING THE SAME

[75] Inventor: Robert S. Langdon, Bedford, N.H.

[73] Assignee: Langdon Medical, Inc., Bedford, N.H.

[21] Appl. No.: 990,900

[22] Filed: Dec. 15, 1992

[51] Int. Cl.⁶ .............................................. G01N 1/00
[52] U.S. Cl. .............................. 73/863.23; 73/864.34; 73/864.73
[58] Field of Search ........... 73/863.23, 863.25, 864.34, 73/864.35, 864.73, 864.11; 128/760, 763, 766–768, 770; 435/30, 31, 35; 604/93, 128, 181, 187, 190, 240, 313; 15/347–352

[56] References Cited

U.S. PATENT DOCUMENTS

| | | | |
|---|---|---|---|
| 965,694 | 7/1910 | Vallant | 15/347 |
| 2,597,715 | 5/1952 | Erikson . | |
| 2,815,621 | 12/1957 | Carter . | |
| 2,845,929 | 8/1958 | Strumia . | |
| 2,999,500 | 9/1961 | Schurer . | |
| 3,085,425 | 4/1963 | Roman | 73/863.25 |
| 3,274,758 | 9/1966 | Parman | 15/347 |
| 3,507,395 | 4/1970 | Bentley . | |
| 3,648,698 | 3/1972 | Doherty . | |
| 3,699,815 | 10/1972 | Holbrook . | |
| 3,773,211 | 11/1973 | Bridgman . | |
| 3,855,997 | 12/1974 | Sauer . | |
| 3,908,657 | 9/1975 | Kowarski | 128/768 |
| 3,965,902 | 6/1976 | Reilly et al. . | |
| 4,013,076 | 3/1977 | Puderbaugh et al. . | |
| 4,275,732 | 6/1981 | Gereg | 15/347 |
| 4,278,456 | 7/1981 | Hug | 15/352 |
| 4,380,845 | 4/1983 | Miller et al. | 15/347 |
| 4,871,662 | 10/1989 | Rosov | 435/30 |

Primary Examiner—Robert Raevis
Attorney, Agent, or Firm—Davis, Bujold & Streck

[57] ABSTRACT

A portable fluid container having an inlet and an outlet for allowing fluid to flow into and out of the portable fluid container. The outlet is completely covered and sealed by a selective filter which only allows gases and minute particles to pass therethrough while retaining liquid and other larger particles within the portable fluid container. The portable fluid container is attached to a cover and the cover seals an opening of a rigid container in which the portable fluid container is placed. The invention also relates to a novel connecting member for interconnecting the fluid container with a desired fluid collection device.

16 Claims, 6 Drawing Sheets

FIG.12

APPARATUS FOR COLLECTING A FLUID SAMPLE FROM A PATIENT AND CONTAINER FOR STORING THE SAME

The present invention relates to an apparatus for collecting a fluid sample from a human or other animal and an improved portable collection container for containing the collected sample.

BACKGROUND OF THE INVENTION

In the medical field, there are a variety of known collection devices presently in use. One such device is shown diagrammatically in FIG. 14 of the drawings. In this known collection device, a collection container 70 is connected, via a flexible conduit 72, with a collection device 74, such as a suction nozzle for insertion into a desired bodily opening for collecting a fluid sample. The container is also connected with a pump 76 via conduit 78. A filter PF may be associated with the conduit 78 to filter undesired particles from the exhaust gases. The outlet of the pump is typically exhausted, via conduit 80, directly in an operating room environment 82.

Figure 14:
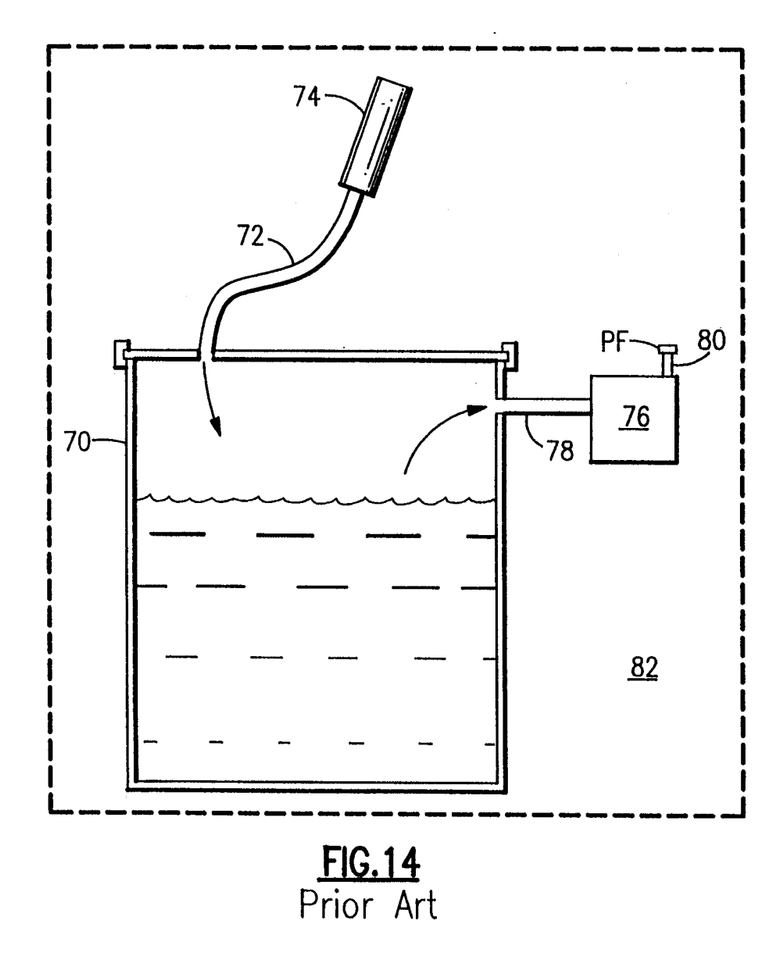
FIG. 14 is a diagrammatic representation showing a prior art fluid collection apparatus.

One of the problems associated with this known collection device is that the interior of the container 70 must be cleaned and sterilized before and/or after each use. A further associated problem is that the exhaust from the pump 76 is discharged directly into the operating room environment 82 or to the environment outside thereof. Accordingly, bacterial cells or particles (typically measuring from about 40 microns to about 0.4 microns in size) and viral cells or particles (typically measuring from about 0.05 microns to about 0.0028 microns in size) may become airborne in the exhaust gases from the pump and discharged directly into the operating room environment where they may be inadvertently inhaled by the patient being operated or the operating room personnel. Consequently, this device has significant health risks associated with its use and such risks are becoming increasingly more important due to AIDS and other serious and/or fatal infections.

Wherefore, it is an object of the present invention to overcome the above noted drawbacks associated with known prior art fluid collection systems.

A further object of the invention is to provide a collection system which substantially minimizes or eliminates the discharge of any viral and bacterial cells or particles into a rigid support container, supporting a fluid collection container, or the operating room environment.

Another object of the invention is to provide a collection system which is relatively inexpensive and simple to manufacture and minimizes the labor associated with repeated use of the fluid collection system.

A still further object of the invention is to provide the collection container which is collapsible so that it is inexpensive to ship to hospitals and the like for use and also facilitates storage of the collection container on site in a relatively small storage area.

Yet another object of the invention is to provide a connector for the portable collection container which is quickly, easily and repeatedly properly connected and disconnected therefrom while still maintaining an adequate fluid sealing connection between the two mated connector components.

A further object of the invention is to provide a connector for the portable collection container which prevents accidental disconnection of the two connected members, once a proper connection therebetween has been achieved.

These and other objects of the invention will be better understood by those skilled in the art by reference to the accompanying drawings and the following description.

SUMMARY OF THE INVENTION

The present invention relates a portable fluid container assembly, for use with a rigid container having an open end, for collection of a desired fluid sample, said portable fluid container comprising a fluid container having an inlet for allowing conveyance of a fluid sample into said fluid container, and an outlet for allowing desired fluid to exit said fluid container; a selective filter completely covering and seally engaging the outlet for allowing, during use, only said desired fluid to exit said fluid container through said outlet while retaining liquid and any desired particles within said fluid container; and means for sealing said fluid container with the open end of the rigid container to facilitate conveyance of a said desired fluid sample through the inlet into said fluid container by application of a partial vacuum to the interior of the rigid container.

The present invention also relates a fluid collection system comprising an open end stationary rigid container; a cover for closing the open end of the stationary rigid container; and a vacuum pump connected with the stationary rigid container for producing a desired partial vacuum within said rigid container, once sealed, the improvement comprising a portable fluid container having an inlet for allowing entry of a desired fluid sample into said portable fluid container, and an outlet for allowing desired fluid to exit said portable fluid container; a selective filter completely covering and seally engaging said outlet for allowing, during use, gases and material under a desired particle size to exit said portable fluid container under the influence of the partial vacuum through said selective filter; and said portable fluid container being formed as a unit with said cover.

The present invention further relates a method of collecting a desired fluid sample comprising the steps of forming, in a fluid container, an inlet for allowing conveyance of a said desired fluid sample into said fluid container, and an outlet for allowing desired fluid to exit said fluid container; completely covering and seally engaging said outlet of the fluid container with a selective filter; positioning said fluid container within an open end of a rigid container and sealing said fluid container with said open end so that said outlet communicates with an interior of the rigid container; connecting the inlet of said fluid container with a collection device; applying a partial vacuum to the interior of the rigid container and sucking, via the applied partial vacuum, a said fluid sample through the collection device and said inlet into said fluid container; and allowing only said desired fluid and gases to exit said fluid container through said selective filter while retaining liquid and desired particles within said fluid container.

BRIEF DESCRIPTION OF THE DRAWINGS

The preferred embodiments of the present invention will now be described, by way of example, with reference to the accompanying drawings, in which.

DESCRIPTION OF THE PREFERRED EMBODIMENTS

Turning now to FIGS. 1–7, a preferred embodiment of a connector for the portable fluid container of the present invention will now be described in detail. The connector 2 comprises a male connector (coupling) member 4 and a female connector (coupling) member 6. The male connector member 4 has a first tube 8 extending through an elongate central portion of that member. The first end of the tube terminates within the connector member 4 at opening 12 positioned to communicate with the female connector member 6 once the two members are interconnected, as described hereinafter. The opposite end of the first tube 8 is connected to a suitable fluid collection device, such as a vacuum inlet of a nozzle (not shown).

Figure 1:
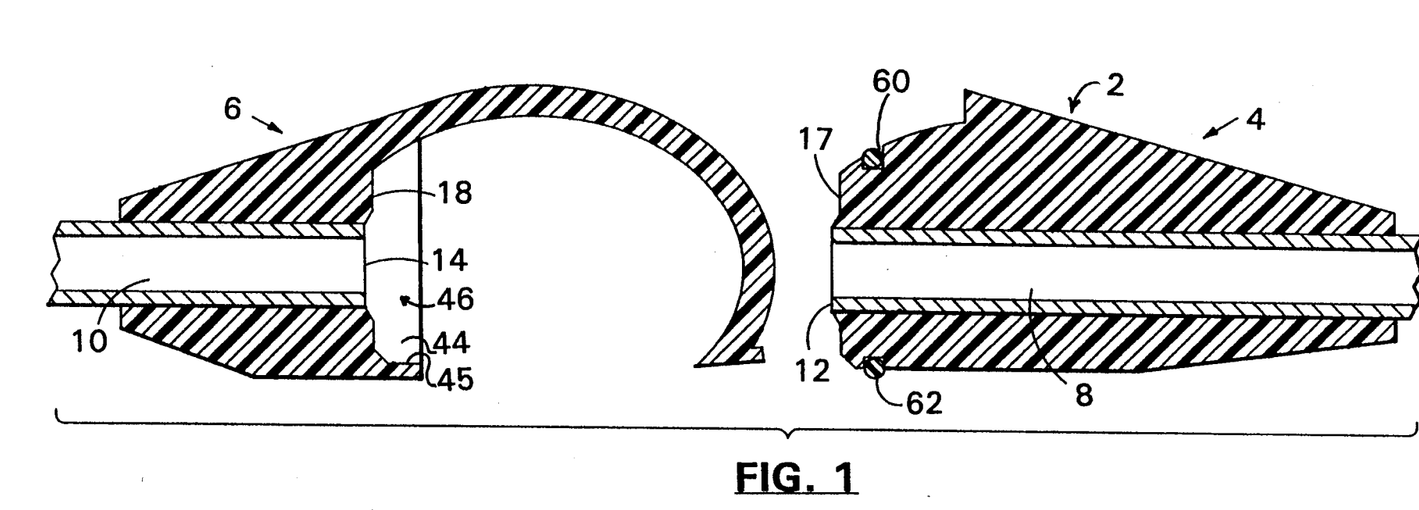
FIG. 1 is a sectional elevation view of a connector for interconnecting tubes, for example, vacuum tubes for use in the present invention.
Figure 7:
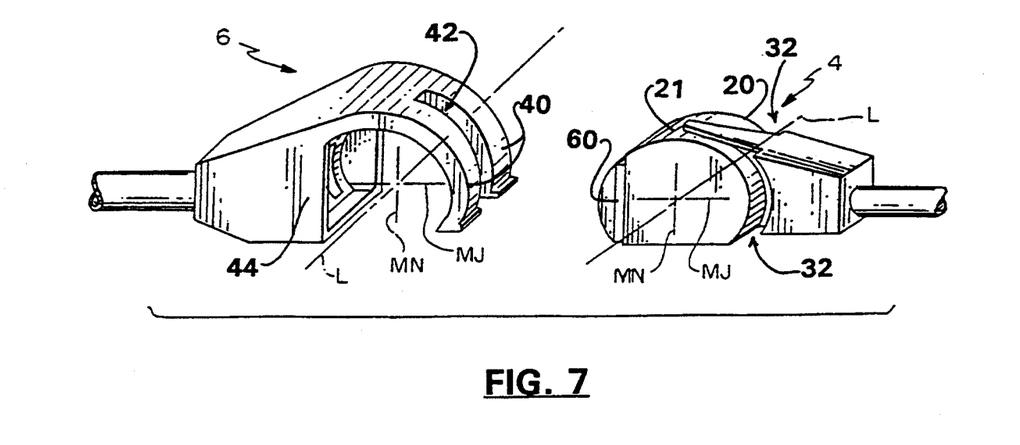
FIG. 7 is a perspective view of the connector, without a seal member in place, according to the present invention.

The female connector member 6 has a second tube extending through an elongate central portion of that member. The tube 10 terminates within the connector at opening 14 positioned to communicate with the tube 8 of the male connector member 4. In order to ensure proper interconnection between the two tubes 8, 10, the tube 8 of the male connector member 4 may extend just outwardly of the nose 17 while the female connector member 6 is provided with a flat face 18 with opening 14 recessed therein whereby the faces 17 and 18 communicate with one another when the connector members 4, 6 are attached together, as describe hereinafter. Alternatively, the tubes could terminate within the connector members 4, 6 and communication therebetween being provided by way of passages (not shown) defined within the connector members 4, 6.

Figure 2:
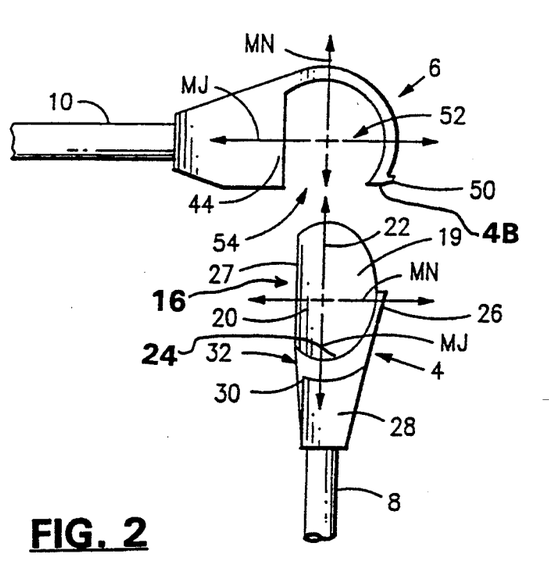
FIGS. 2 through 5 show sequentially the steps required for interconnecting male and female connector members.

The male connector member 4 further includes a main housing 16 comprising an semi-elliptical or semi-oval-shaped portion 19, defining a major axis MJ, a minor axis MN and a longitudinal axis L, having a pair of opposed semi-elliptical or semi-oval-shaped sidewalls 20 (see FIGS. 1, 2 and 7). The pair of semi-oval-shaped sidewalls 20 diverge so as to provide a gradual expansion of the semi-oval-shaped portion 19 along the major axis MJ from a relatively narrow end 22, having opening 12, to a relatively wide end 24. A top surface of the main housing 16 is provided with a tapered central alignment ridge or protrusion 26. A lower surface of the main housing 16 is a flat surface 27, the purpose of which will be described hereinafter. A housing extension 28 is provided on the male connector member 4 adjacent the wide end 24 and defines, with the main housing 16, two opposed grooves 32. An abutment edge 30 is positioned adjacent an edge of the housing extension 28 remote from the alignment protrusion 26 but adjacent the wide end 24 of the main housing 16, the purpose of which will also be described hereinafter.

The female housing 18 has a pair of resilient parallel legs 40 each terminating in an end portion 48. Each of the legs 40 has an semi-elliptical or semi-oval-shaped longitudinal shape. A tapered open-ended slot 42 is formed between the two parallel legs 40 for receiving the alignment ridge or protrusion 26. The inner end of the open ended slot 42 acts as a stop for preventing further pivoting movement of the male connector member with respect to the female connector member 6. Two opposed sidewalls 44 are provided adjacent the second opening 14 to form a recess 46 for receiving the tapered end 22 of the male connector member 4. The spacing between the two opposed sidewalls 44 is such that the sidewalls 44 will intimately engage a portion of the oval-shaped sidewalls 20 of the male connector member when the tapered end 22 is accommodated within the recess 46. A flat step 45 is formed between the two sidewalls 44 along an edge of the recess 46 remote from the legs 40. The purpose of this flat step will also be described hereinafter. The female housing 18, including the two legs 40, form an interior semi-elliptical or semi-oval shaped cavity 52, defining a major axis MJ, a minor axis MN and a longitudinal axis L, with access to this area being provided by way of an opening 54.

The opening 54 is about as wide as the dimension of the semi-oval-shaped portion 19 along its minor axis MN so that the legs 40 are biased outwardly slightly upon insertion of the semi-oval-shaped portion 19 into the semi-oval-shaped cavity 52.

The oval-shaped portion 19 is of substantially the same size as the semi-oval-shaped cavity 52 so that a close intimate engagement between the two connector members is achieved once they are interconnected. Due to their similar size, the opening 54 is forced open as the portion 19 of the male connector member 4 rotates within the cavity 52 of the female connector member 6 and then returns substantially to its initial position upon completion of the rotation to hold the male connector member 4 captive.

Figure 3:
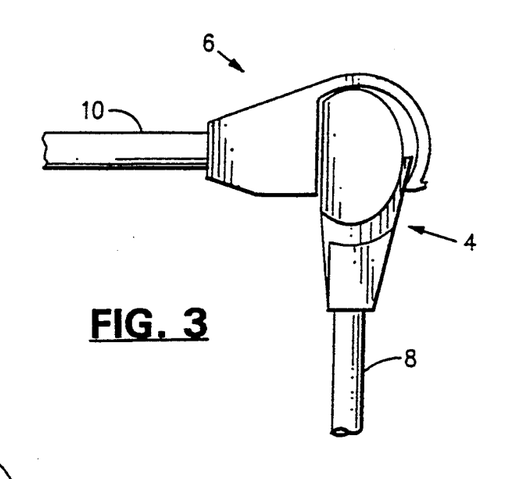
Figure 4:
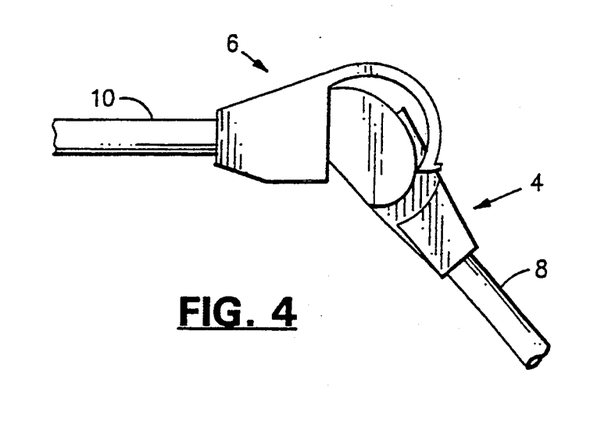
Figure 5:
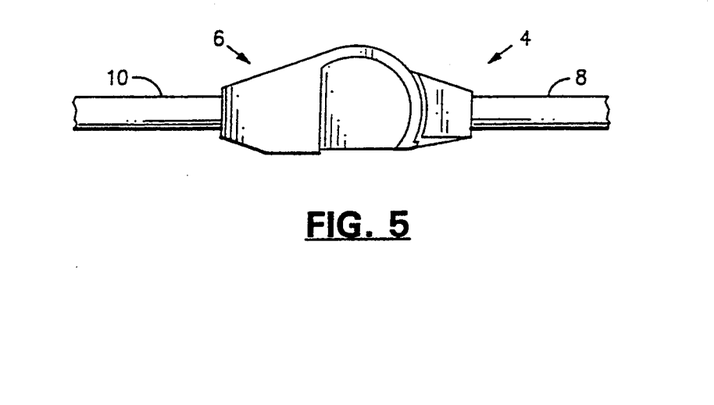

Attachment of the male and female connector members of the present invention will now be described with reference to FIGS. 2–5. The connector members are first disposed at 90° with respect to one another with the tapered end 22 of the male connector 4 located adjacent the opening 54 of the female connector member 6, i.e. the major axis MJ of the male connector member 4 being aligned with the minor axis MN of the female connector member 6 (FIG. 2). The male connector member 4 is then moved toward the female connector member 6 and passed through the opening 54, into the semi-oval shaped cavity 52 of the female connector 6 until the tapered end 22 abuts against an inner surface of the legs 40 (FIG. 3). This inserting movement causes the end portions 48 of the legs 40 to be biased outwardly slightly by the exterior surface 21 of the semi-oval-shaped portion 19 as the male connector member 4 enters into the semi-oval-shaped cavity 52 of the female connector member 6. After the tapered end 22 abuts against the inner surface of the legs 40, the male connector member 4 is rotated 90 degrees with respect to the female connector member 6 about the longitudinal axis L. During this pivoting movement, an inner surface of the end portions 48 of the legs 40 slide along the smooth exterior surface 21 of the semi-oval portion 19 while the alignment protrusion 26 is guided by the open ended slot 42, between the two legs 40, to ensure proper alignment of the two connector members 4, 6. Once the male connector member 4 has been pivoted approximately 45 degrees with respect to the female connector member 6 (FIG. 4), the end portions 48 of the legs engage and are guided by the grooves 32 to assist further with proper alignment of the two connection members. After the connector members 4, 6 are rotated into the position shown in FIG. 4, the bottom flat surface 27 of the male connector member 4 engages the step 45 of the female connector member 6. Thereafter, the flat surface 27 pivots about the step 45 until the two connector members are completely engaged (FIG. 5). Once complete engagement has occurred, the tapered end 22 of the male connection member 4 is accommodated within the recess 46 and this achieves proper alignment of and communication between the two tubes 8, 10. Due to the semi-oval shaped configuration of the semi-oval-shaped portion 19 and semi-oval shaped cavity 52, this engagement resiliently prevents the members from rotating relative to one another from the position shown in FIG. 5 so that the two connection members are maintained in longitudinal alignment with one another until disconnection of the two connector members is desired.

Figure 6:
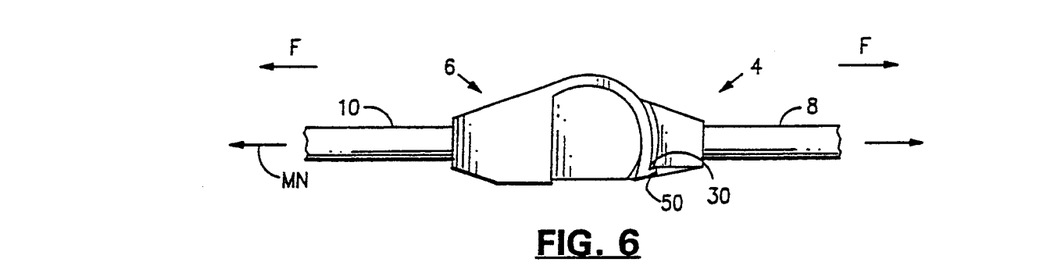
FIG. 6 shows the locking action of the present invention for preventing separation of the two connector members once properly engaged.

When properly engaged, the two connection members are prevented from becoming disengaged from one another by the two abutment edges 30 carried by the housing extension 28 of the male connector member 4 and the two abutment flanges 50 carried by the end portions 48 of the legs 40 (FIG. 6). When a disconnecting force F is applied along the major axes MN of the connection device, the legs 40, due to their resilience, will tend to straighten slightly adjacent the end portions 48 so that the abutment flanges 50 are brought into engagement with the abutment edges 30 and this locking mechanism prevents any further disengaging movement of the two connection members while under such tension.

It is important to note that the width of the grooves 32 must be slightly larger that the thickness of the end portions 48 of the legs 40, including flanges 50, so that connection and disconnection can easily occur while still retaining the locking feature of the present invention.

To disconnect the connection members, the male connection member is rotated 90 degrees relative to the female connector member 6, reversing the steps shown in FIGS. 2-5, so that male connector member 4 can thereafter be removed through the opening 54 of the female connector member 6.

Turning now to FIGS. 1 and 7, a continuous peripheral groove 60 is formed in the male connector member 4, adjacent the tapered end 22, spaced from the periphery of the first tube 8. A sealing member 62 (FIG. 1), such as an elastomeric O-ring or the like, is accommodated within the peripheral groove 60. The peripheral groove 60 and the seal member 62 combine with the interior surface of the recess 46 to provide a fluid tight seal between the two connector members 4, 6 once properly engaged. The tubes 8, 10 may be sealed, by an adhesive or the like, with respect to the housing to prevent fluid from entering or leaking through a gap between those members. This sealing arrangement provides a sealed communication between the tubes 8, 10. In addition to being useful for vacuum (sub-atmospheric pressures) the connection of this embodiment is also suitable for pressurized flows provided leakage past the seal is not exceeded in an unacceptable manner.

Figure 8:
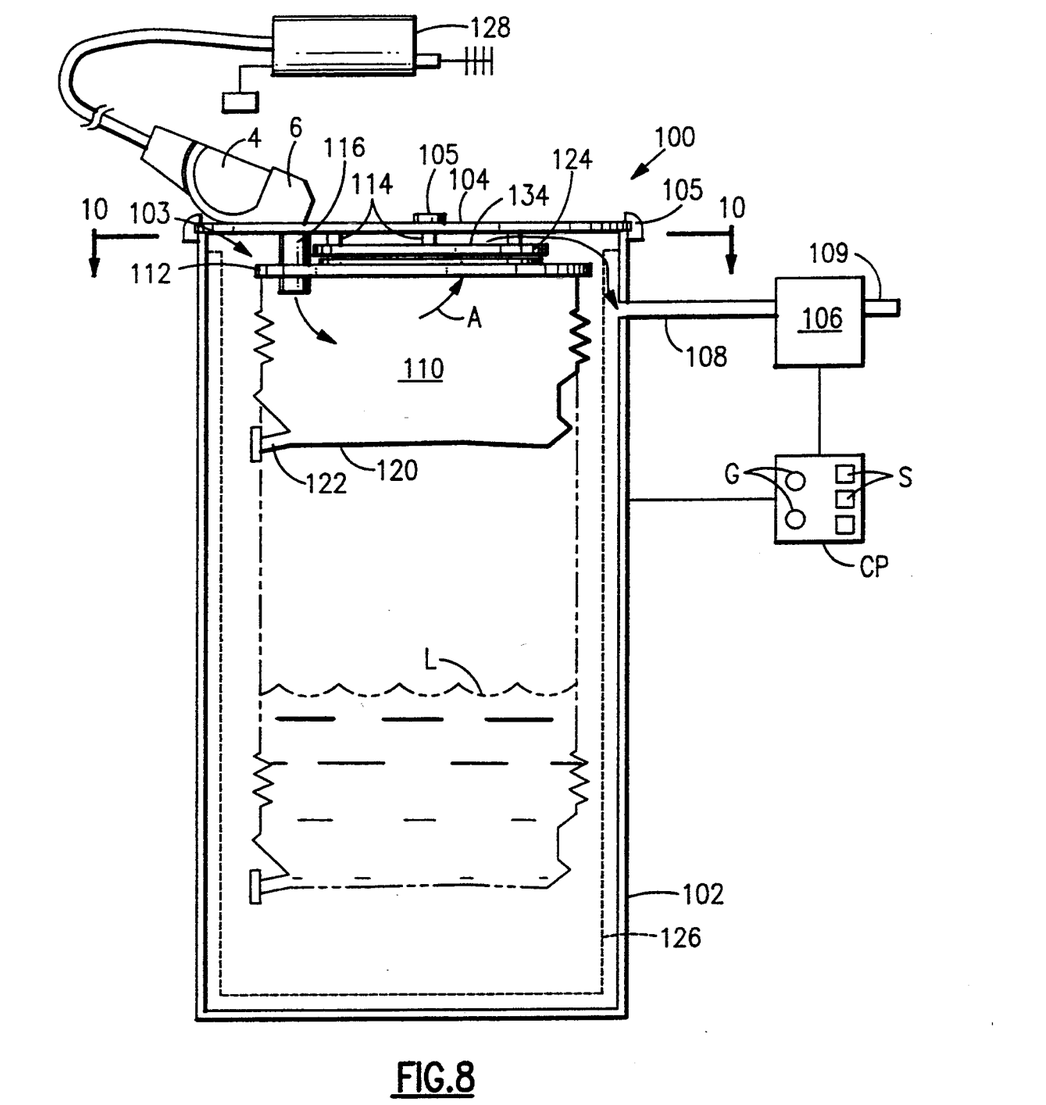
FIG. 8 is a diagrammatic representation of the fluid collection apparatus according to the present invention.

Turning now to FIG. 8, the fluid collection apparatus 100, according to the present invention, will now be described in detail. The apparatus 100 comprises an open end stationary rigid container 102 having a removable cover 104, which may be latched or clamped to the opening 103 of the stationary rigid container 102 by suitable releasable attachment means 105, e.g. a plurality of equally spaced latches arranged around the circumference of the opening 103. The releasable attachment means 105 must releasably and tightly secure the cover to seal the cover to the stationary rigid container so that the necessary partial pressures, required for effective operation of the apparatus, may be achieved. The opening 103 may be provided with a circular gasket or seal 107 located to engage the removable cover 104 when in its closed position to provide the necessary seal between these two members.

The stationary rigid container 102 communicates with a vacuum pump 106, via conduit 108, and the exhaust gases from the pump 106 are discharged via conduit 109 into the environment. During use of the apparatus, the vacuum pump preferably generates approximately 15 inches of mercury below atmospheric pressure in the stationary rigid container 102.

Figure 11:
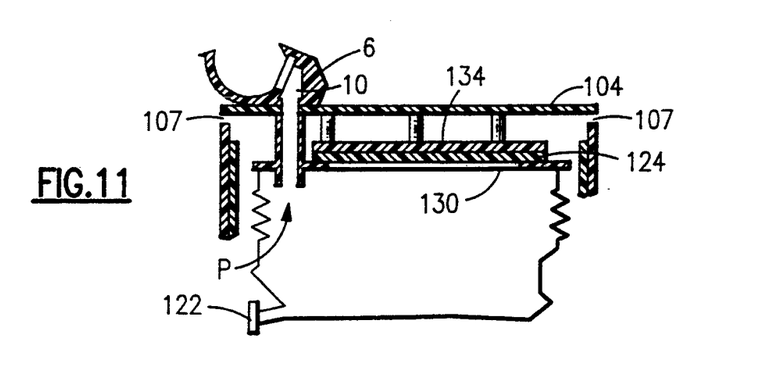
FIG. 11 is a diagrammatic partial sectional view along section line 11—11 of FIG. 10.

In the embodiment shown in FIG. 8, the removable fluid container 110 is unitary with the removable rigid cover 104. The container 110 comprises a rigid member 112 spaced from a bottom surface of the cover 104 by a plurality of equally spaced spacer members 114. A female connector member 6 is attached to the opposite surface of the cover 104 and a cylindrical conduit 116, having a passageway P therein (FIG. 11), is connected to and extends from the rigid member 112, through the cover 104 and communicates with the tube 10 of the female connector member 6 to provide communication between the tube 10 and the interior of the removable fluid container (FIG. 11).

An open end flexible collapsible bag 120 is adhesively secured, ultrasonically welded, or attached by other suitable known means, around the perimeter of the rigid member 112 to form a sealed engagement therewith. The lower portion of the flexible, collapsible bag 120 is provided with a break-off valve 122 for removing a desired liquid sample after collection of the fluid sample is achieved. The rigid member 112 is provided with a central circular outlet 130, having a diameter of about 120 mm, which is covered and sealed by a selective filter 124 secured to the rigid member 112 on the side opposite the collapsible bag 120. A spider 134, which will be discussed in greater detail hereinafter, secures the selective filter 124 to the rigid member 122. The selective filter 124, depending on the filter material employed, allows gases and minute particles, e.g. particles having a size smaller than a desired particle size, to pass therethrough while filtering larger particles, viruses, bacteria and liquid. A more detailed explanation of the selective filter 124 follows hereinafter.

The collapsible bag 120 is typically formed from a flexible plastic film, preferably polyvinylchloride or other similar sterilizable material. If desired, a suitable shutoff valve, capable of withstanding a pressure of approximately 15 inches of mercury below atmosphere without any leakage, may be used instead of the break off valve 122.

A rigid perforated or meshed element 126, such as a screen or perforated cylindrical sleeve, maintains the collapsible bag 120 in a spaced relationship from the interior of the stationary rigid container 102. This meshed element prevents the collapsible bag 120 from being sucked into and/or plugging the inlet of conduit 108 during operation of the apparatus. The rigid mesh element 126 also ensures an adequate air flow around the collapsible bag 120 to substantially equalize pressure inside and outside of the bag, during use of the apparatus. This assists the collapsible bag 120 with expanding and falling, under gravity toward the base of the stationary rigid container 102, as liquid L gradually collects within the collapsible bag 120.

Prior to use, the male connector member 4 is connected to the female connector member 6. The male connector member 4, in turn, has a suitable collection device 128, such as a nozzle or a brush/scope/suction combination for removing or sucking blood or another desired fluid sample from a patient during a medical procedure, connected to the opposite end of the second tube.

Figure 9:
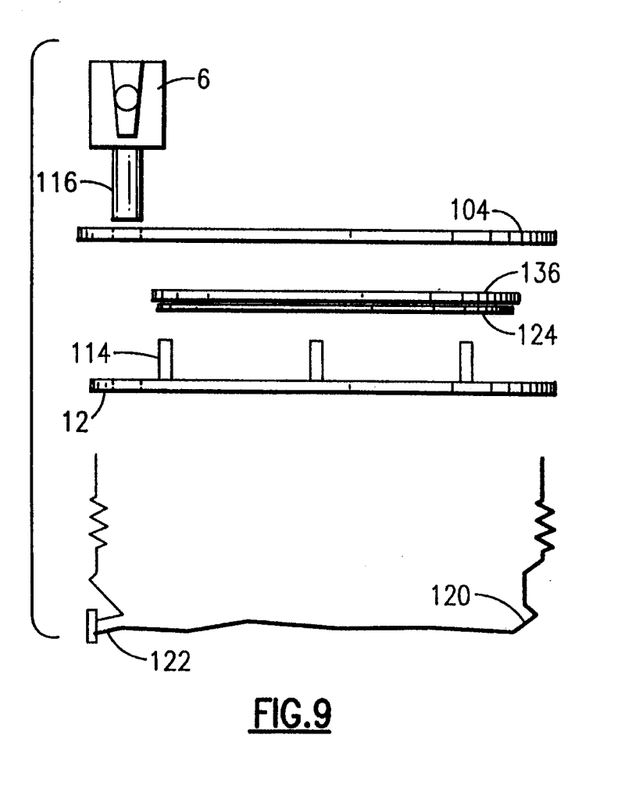
FIG. 9 is a diagrammatic representation of the portable collection container according to the present invention.
Figure 10:
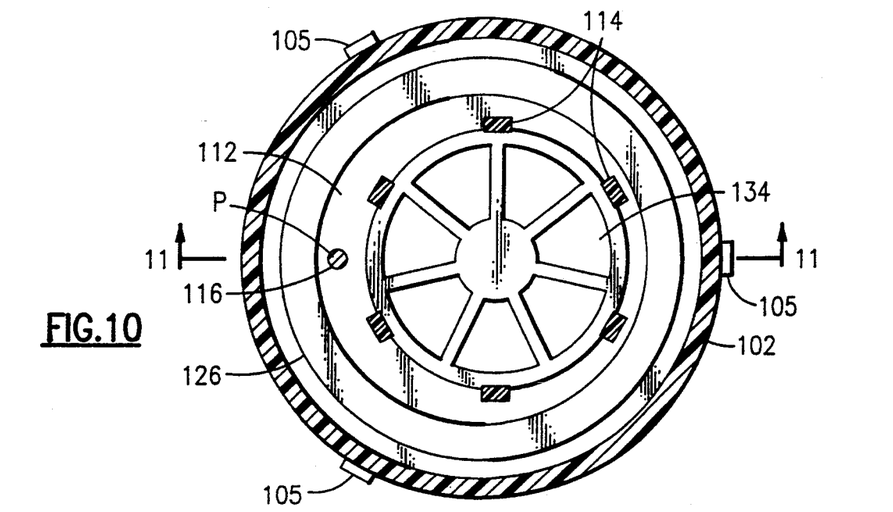
FIG. 10 is a diagrammatic sectional view along line 10—10 of FIG. 8.

Turning now to FIGS. 9-11, a more thorough description of the selective filter 124 will be provided. The selective filter 124 covers the entire outlet 130 and is adhesively secured, ultrasonically welded or securely fastened thereto to ensure that all fluid being drawn out by the vacuum pump 106 passes through the selective filter, without any leakage between the rigid member 112 and the selective filter 124. A support element such as the rigid spider 134, having spokes and made of plastic or the like, is also secured to the rigid member 112 and sandwiches the selective filter 124 therebetween. The spider 134 provides the selective filter 124 with sufficient support, during use of the apparatus, to assist in preventing the selective filter 124 from being ruptured.

The selective filter 124 is chosen to prevent passage of desired particles, e.g. desired viral and bacterial cells and/or particles, from the stream of the fluid sample evacuated from the patient. A variety of suitable selective filters, depending upon the desired virus, bacteria, particles, etc., to be removed, are manufactured by Millipore Corporation of Bedford, Mass. One such suitable selective filter manufactured by that company is sold under the trademark VIRESOLVE(®) (70 or 180).

With a 4 micron selective filter positioned over the 120 mm diameter outlet in the rigid member 112, the inventor was, using a suction of about 15 inches of Mercury, able to achieve a fluid collection flow rate of about 1.5 cc/second through the fluid collection apparatus according to the present invention. With a 2.8 micron selective filter positioned over the 120 mm diameter outlet in the rigid member 112, the other parameters being the equal, a fluid collection flow rate of about 1.2 cc/second was achieved. It is to be appreciated that, once the selective filter is chosen for a particular application, the flow rate thorough the apparatus may be varied by varying the area of the outlet 130, e.g. increasing the area of the outlet to increase the flow rate.

Figure 12:
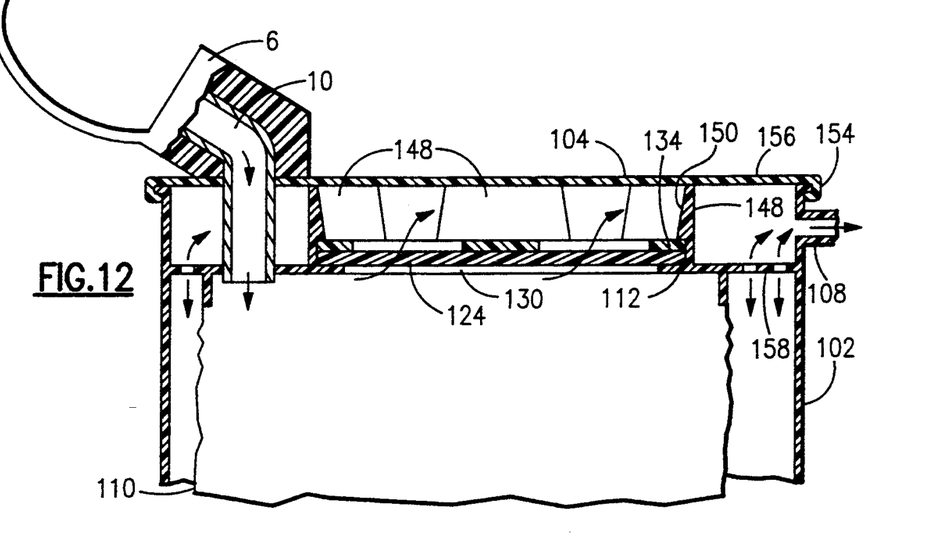
FIG. 12 is a diagrammatic partial sectional view, similar to FIG. 10, of a second embodiment of the arrangement for securing the selective filter to the rigid member.

Turning now to FIG. 12, a second embodiment for attaching the selective filter 124 to the rigid member 112 will be described. In this embodiment, a plurality of upstanding hook-shaped members 148 are equally spaced about the perimeter of the outlet 130. The hooked portion 150 of each member is spaced from the rigid member by a distance slightly less than the thickness of the selective filter 124 and the spider 134 so that the selective filter is compressed tightly against the rigid member and provides a perimeter seal entirely around the outlet 130. It will be appreciated that the hook portions here are formed integrally with the spacer members although separate spacers could be utilized. Further, the hook shaped members 148 may be integrally formed with the rigid member 112 or adhesively secured, ultrasonically welded or attached thereto by other suitable known means.

In the embodiment of FIG. 12, the cover 104 is formed with an annular peripheral lip 154 which resiliently engages a radially protruding rim 156 of the rigid container 102 defining the upper open end thereof. This engagement provides the attachment for the cover to the container and the seal therebetween in much the same manner as plastic top reseal coffee cans, etc. In this embodiment, the rigid mesh element 126 is omitted in favor of a peripheral extension flange 158 of the rigid member 112 to bring it into close proximity with the interior of the rigid container 102. This proximity providing a space which is small enough to prevent material of the bag 110 from being sucked into the outlet 108 which, in this embodiment, is placed longitudinally between the rigid cover 104 and the rigid member 112 when the cover 104 is attached to the container 102. Equalization of pressure inside and outside of the bag within the container 102 is achieved by the provision of at least one opening, preferably a large plurality of openings, passing through the flange 158 in the space between the cover 104 and member 112 outside of the bag 110 adjacent the interior perimeter of the container 102. In this embodiment, the spider 134 comprises an annular perimeter member connected to a central hub by plurality of spokes of sufficient strength to maintain the selective filter 124 in position when the apparatus is subjected to a specimen collect vacuum. It will be appreciated that the perforated flange, which prevents the bag from being sucked into the outlet 108, could be replaced by an annular mesh member surrounding the outer perimeter of the rigid member 112 or by a series of spokes. The design of which will be apparent to those skilled in the art.

It will also be appreciated by those skilled in the art that the means by which suction of the bag 110 into the outlet 108 may be avoided and can be achieved by a mesh cone or dome overlying the outlet 108 or by a lip on the outlet 108 which extends into the container 102 to a location preventing access of the opening to that outlet by the bag 110.

The components attached together for mounting on the container 102 may be integrally formed, ultrasonically welded or adhesively attached together or mechanically interconnected, etc. as will be apparent to those skilled in the art.

Figure 13:
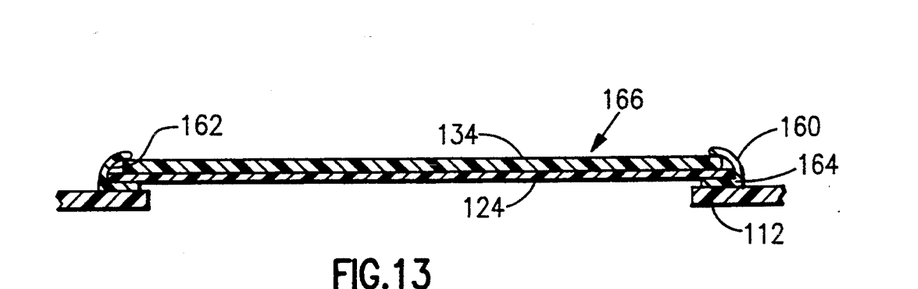
FIG. 13 is a diagrammatic partial sectional view, similar to FIG. 10, of a third embodiment of the arrangement for securing the selective filter to the rigid member.

In FIG. 13, a third embodiment for securing the selective filter to the rigid member can be seen. In this embodiment, an annular clamping member 160 is utilized for attaching the selective filter 124 and the spider 134 to the rigid member 112. The annular clamping member 160 is provided with an inner annular recess 162 which has a width slightly less than the thickness of the selective filter and the spider to be accommodated therein. In this embodiment, the selective filters is first position within the annular recess 162 and abuts an annular end face 164. Thereafter, the clamping member 160 is slightly deformed into a cupped configuration and passed to space 166 and then it is allowed to assume its original undeformed position thereby stretching and compressing the selective filter 124 against end face 164. When the filter 124 and the spider are properly positioned within the annular recess 162, the annular clamping member 160 is then adhesively bonded, ultrasonically welded, or permanently secured, by any other attachment means well known in this art. Alternatively, the annular clamping member 160 may be formed integrally with the rigid member.

It is to be appreciated that other known arrangements may be used for securing the selective filter to the rigid member 112 to completely seal the open end. Such other arrangements will be well known to those skilled in the art and are not discussed in detail any further.

With reference to FIG. 8 of the drawings, operation of the apparatus will now be explained. The removable fluid container 110 is positioned within the open end of the stationary rigid container 102 so that the collapsible bag is located within the rigid container while the removable cover engages the opening 103. Thereafter, the attachment means 105 are locked to secure the cover 104 to the rigid container 102. The male connector member 4, having a collection device 128 connected to the opposite end thereof, is connected to the female connector member 6. The apparatus is then ready for use.

The operator first activates a switch S of the control panel CP which activates on the pump 106 of the fluid collection apparatus.

A vacuum and/or pressure gauge G may be provided on the control panel to indicate the vacuum and/or pressure within the stationary rigid container 102.

The collection device 128 is then positioned at a desired location where a fluid sample is to be collected, e.g. sucking blood from an incision during an operation, collecting a cytology sample from a desired location in a bladder, cell samples from an irrigated dry site, etc. The pump 106 draws the fluid, e.g. blood, cell bearing urine, etc., into an inlet of the device 128, and conveys this fluid through tubes 8 and 10 and conduit 116 into the collapsible bag 120. As the collected fluid, liquid and gases, flow out of the conduit 116 into the interior of the container 110, the liquid remains in the bag 110 while air and other gases flow through the selective filter 124 (see arrow A). Any particles, cells, viruses, bacteria, etc. which are not of a sufficient small size to pass through the filter, e.g. having a molecular weight greater than 70,000 or having a size greater than 0.025 microns, are retained by the filter in the bag. The air and other gases which pass through the selective filter then enter the conduit 108 and are exhausted by the pump 104 through discharge outlet conduit 109 as desired. Accordingly, the desired harmful viral and bacterial contaminates and the like are filtered by the selective filter 124 and trapped within the bag. By this arrangement, the exhaust from outlet 109 can be discharged directly into the operating room environment without any appreciable health risks being associated with such discharge.

As the liquid collects in the bag 120, the bag will gradually unfold and expand due to the weight and volume increase of the collected liquid. The rigid mesh element 126 maintains the collapsible bag substantially centered within the stationary container 102 and prevents the conduit 108 from being blocked by the flexible bag 120.

Once a suitable fluid sample is collected or the container 110 is substantially full, the pump 106 is turned off and the removable fluid container 110 is removed from the stationary rigid container 102. In order to obtain a desired liquid sample, the break off valve 122 is cut by a user and this allows a portion of the liquid to flow out through the valve 122. Once a sufficient sample is transferred to a desired sampling device, such as a test tube or the like, the valve can be pinched closed or the removable fluid container 110 tilted so that the break off valve 122 is raised above the fluid level and further flow through the valve will not occur. The removable fluid container 110 is then transported in the closed or tilted state to a suitable liquid disposal site so that all of the remaining liquid can be drained from the removable fluid container 110 and properly disposed. After this has occurred, the collapsible container can then be collapsed and disposed of with other solid hospital waste.

It is to be appreciated that the fluid collection apparatus of the present invention can also be employed to supply a fluid L, such as a saline solution, to a desired bodily location during an operation. For such use, the apparatus is essentially the same as discussed above except that the pump operates (e.g. in the reverse direction) to pressurize the stationary rigid container. In addition, the portable fluid container 110, for this embodiment, does not require a space relationship from the cover 104 or the selective filter 124. The portable fluid container 110 is first filled with the desired fluid and then connected to the stationary rigid container 102, as with the first embodiment. As the rigid container becomes pressurized, the pressure acts on the exterior surface of the fluid container thereby compressing its contents and gradually forcing and dispensing the liquid L from the collapsible bag. The dispensed fluid is conveyed out through the passageway P of the conduit 116, the tubes 10 and 8 out to the outlet of the device 128 and discharged where desired.

It is to be appreciated that the apparatus may be equipped with two separate rigid containers, one for withdrawing a sample and the other for applying a fluid sample. In such instance, an appropriate vacuum or pressurized pump is associated with each container and the control panel CP is provided with two separate switches and a separate pressure/vacuum gauge is connected with each rigid container to indicate, during use, the pressure/vacuum therein.

Since certain changes may be made in the above apparatus without departing from the spirit and scope of the invention herein involved, it is intended that all matters contained in the above description and/or shown in the accompanying drawings shall be interpreted as illustrating the inventive concept herein involved and shall not be construed as limiting the invention.

I claim:

1. A portable fluid container assembly, for use with a rigid container having an open end, for collection of a desired fluid sample, said portable fluid container assembly comprising:
- a fluid container having an inlet for allowing conveyance of a fluid sample into said fluid container, and an outlet for allowing desired fluid to exit said fluid container;
- a selective filter completely covering and sealingly engaging said outlet for allowing, during use, only said desired fluid to exit said fluid container through said outlet while retaining liquid and any desired particles within said fluid container; and
- means for sealing said fluid container with the open end of the rigid container to facilitate conveyance of a said desired fluid sample through said inlet into said fluid container by application of a partial vacuum to the interior of the rigid container; wherein
- a portion of said fluid container is rigid and said outlet is formed in that rigid portion; and
- the remainder of said fluid container is flexible and said flexible portion is permanently sealingly attached to said rigid portion to form said container assembly.

2. A portable fluid container assembly according to claim 1, wherein said flexible portion has means permitting removal a desired liquid sample once collected in said container assembly.

3. A portable fluid container assembly according to claim 1, wherein said means for sealing said fluid container with the open end comprises a cover for sealingly engaging a said rigid container, and
- said rigid portion is connected to but spaced from said rigid cover by a plurality of spacer members.

4. A portable fluid container assembly according to claim 3, wherein a first fluid coupling member is secured to said cover on a surface thereof remote from said rigid portion, and
- a conduit, having a passageway formed therein, extends from said fluid coupling member to rigid portion to provide a fluid path from said first fluid coupling member to the interior of said fluid container.

5. A portable fluid container assembly according to claim 4, wherein said fluid coupling member comprises one of a mating male connector member and female connector member;
- said female connector member defining a cavity, of generally oval cross-section, defining a major axis, a minor axis and a longitudinal axis, having an opening thereto remote from said major axis and said longitudinal axis, the oval cross-section subtending an angle in excess of 180° about said longitudinal axis; and
- said male connector member defining a body portion, of generally oval cross-section, defining a major axis, a minor axis and a longitudinal axis, shaped to intimately fit within said generally oval cavity of said female connector member, the opening being narrower then the dimension of the body portion along its major axis;
- and when said body portion of said male connector member is passed through the opening of the female connector member into said generally oval cavity and rotated so that their major axes are substantially aligned with one another, said male connector member is resiliently retained by the female connector member with conduit means of said female and male connector members in engagement with one another hereby forming said releasable interconnection between said conduit means of said female and male connector members, and the conduit means of the connector member forming the first fluid coupling member being a part of said conduit.

6. A portable fluid container assembly according to claim 5, wherein the conduit means of the other of the mating male and female connector members is connected to the assembly for receiving a said desired fluid sample collected thereby.

7. A portable fluid container assembly according to claim 1, wherein a rigid support supports said selective filter opposite said outlet to support said selective filter, during use, in said sealing engagement with said outlet and to maintain the integrity of said selective filter.

8. A portable fluid container assembly according to claim 7, wherein a plurality of latch members, secured to said rigid portion, bias both said rigid support and said selective filter against said rigid portion to provide a fluid tight seal between said selective filter and said outlet of said rigid member.

9. A portable fluid container assembly according to claim 7, wherein said rigid support and said selective filter are accommodated within an inner annular recess of an annular member, and said annular member is one of secured to and integral with said rigid member about the periphery of said outlet.

10. A portable fluid container according to claim 9, wherein said annular member is a discontinuous ring member.

11. A portable fluid container assembly according to claim 10, wherein said selective filter only allows material having a sufficiently small size to pass therethrough.

12. A fluid collection system comprising an open end stationary rigid container;
- a portable fluid container assembly, for use with a rigid container having an open end, for collection of a desired fluid sample, said portable fluid container assembly comprising:
- a fluid container having an inlet for allowing conveyance of a fluid sample into said fluid container, and an outlet for allowing desired fluid to exit said fluid container;
- a selective filter completely covering and sealingly engaging said outlet for allowing, during use, only said desired fluid to exit said fluid container through said outlet while retaining liquid and any desired particles within said fluid container; and
- means for sealing said fluid container with the open end of the rigid container to facilitate conveyance of a said desired fluid sample through said inlet into said fluid container by application of a partial vacuum to the interior of the rigid container; wherein
- a portion of said fluid container is rigid and said outlet is formed in that rigid portion; and
- the remainder of said fluid container is flexible and said flexible portion is permanently sealingly attached to rigid portion to form said container assembly;
- a cover for closing the open end of the stationary rigid container; and
- a vacuum pump connected with the stationary rigid container for producing a desired partial vacuum within said rigid container, once sealed,
- said portable fluid container being formed as a unit with said cover.

13. A fluid collection system according to claim 12, wherein a rigid mesh element is provided within the stationary rigid container to space said portable fluid container from an inner surface of said stationary rigid container.

14. A fluid collection system according to claim 12, wherein an inlet to said vacuum pump is located adjacent the open end of said stationary rigid container.

15. A portable fluid container assembly according to claim 12, wherein said rigid portion is connected to but spaced from said cover by a plurality of spacer members.

16. A portable fluid container assembly according to claim 12, wherein a rigid support supports said selective filter opposite to said outlet to support said selective filter, during use, in said sealing engagement with said outlet and to maintain the integrity of said selective filter.

* * * * *